United States Patent [19]

Chauvin et al.

[11] Patent Number: 5,723,712
[45] Date of Patent: Mar. 3, 1998

[54] CATALYTIC COMPOSITION FOR BIPHASE CATALYSIS, IN PARTICULAR USING NICKEL COMPLEXES, AND A PROCESS FOR THE OLIGOMERIZATION OF OLEFINS

[75] Inventors: Yves Chauvin, Le Pecq, France; Roberto de Souza, Porto Alegre, Brazil; Helene Olivier, Rueil Malmaison, France

[73] Assignee: Institut Francais du Petrole, Rueil-Malmaison, France

[21] Appl. No.: 676,670

[22] Filed: Jul. 10, 1996

[30] Foreign Application Priority Data

Jul. 11, 1995 [FR] France ................. 95/08492

[51] Int. Cl.$^6$ ................. C07C 2/30
[52] U.S. Cl. ................. 585/513; 585/512; 585/527; 585/530; 585/531; 502/117; 502/129; 502/154
[58] Field of Search ................. 502/117, 129, 502/154, 113, 114; 585/512, 513, 530, 531, 527

[56] References Cited

U.S. PATENT DOCUMENTS

| | | |
|---|---|---|
| 3,038,892 | 6/1962 | Coover, Jr. ................. 526/124.1 |
| 3,125,558 | 3/1964 | Hagemeyer, Jr. et al. ........ 526/124.1 |
| 4,187,197 | 2/1980 | Kabanov et al. ................. 252/431 |
| 4,362,650 | 12/1982 | Chauvin et al. ................. 585/513 X |
| 4,996,273 | 2/1991 | Van Der Huizen ................. 526/177 |
| 5,414,160 | 5/1995 | Sato et al. ................. 585/513 X |

FOREIGN PATENT DOCUMENTS

| | | |
|---|---|---|
| 0 009 035 | 3/1980 | European Pat. Off. . |
| 0 470 794 | 2/1992 | European Pat. Off. . |
| 0 531 174 | 3/1993 | European Pat. Off. . |

*Primary Examiner*—Fred Teskin
*Attorney, Agent, or Firm*—Millen, White, Zelano, & Branigan, P.C.

[57] ABSTRACT

A novel catalytic composition comprises a mixture of lithium halide, a hydrocarbylaluminium halide and at least one compound of a catalytic element, in particular a nickel complex. The invention also concerns a process for the oligomerisation and co-oligomerisation of olefins catalysed by said composition. The catalytic mixture, which is liquid at the start of the reaction, is gradually transformed into a solid which is then readily separated from the reaction products.

19 Claims, No Drawings

/ 1

CATALYTIC COMPOSITION FOR BIPHASE CATALYSIS, IN PARTICULAR USING NICKEL COMPLEXES, AND A PROCESS FOR THE OLIGOMERIZATION OF OLEFINS

FIELD OF THE INVENTION

An object of the present invention is to provide a novel catalytic composition and its use for the dimerisation, codimerisation, oligomerisation and co-oligomerisation of olefins, the composition comprising at least one lithium halide, at least one hydrocarbylaluminium halide and at least one compound of a catalytic element, in particular a nickel compound.

BACKGROUND OF THE INVENTION

A large number of catalytic systems based on nickel compounds are known for the oligomerisation of olefins. Such catalysts can be heterogeneous, i.e., totally insoluble in compatible organic solvents or in olefins and their oligomerisation products; examples are nickel sulphate deposited on an alumina, nickel chloride deposited on silica-alumina, and nickel-exchanged zeolites. Such catalysts can also be homogeneous, i.e., dissolved in an organic solvent such as chlorobenzene or dissolved in the oligomerisation products. Such catalysts can be used in organochloroaluminates based on quaternary ammonium salts, thus constituting a biphase liquid-liquid system as described in French patent FR-A-2 659 871.

All such catalysts have inherent disadvantages in their use. Conventional heterogeneous catalysts cannot use the "phosphine effect" as described by G. Wilke et al. in Angewandte Chemie, International Edition, 1966, 5, 151, and suffer limitations due to mass transfer (loss of selectivity) or heat transfer. With homogeneous catalysts, the catalyst is poorly used, leaving the reactor when it is still active. Product separation is also a problem.

SUMMARY OF THE INVENTION

It has now been discovered that a liquid mixture of at least one lithium halide with at least one hydrocarbylaluminium halide, into which at least one catalytic element and at least one hydrocarbon phase has been introduced, can be transformed into a solid catalyst which separates from the hydrocarbon phase.

The liquid catalytic composition, a liquid mixture plus catalytic element, which is present at the moment when the hydrocarbon phase is initially introduced, is catalytically active for biphase liquid-liquid catalysis, can transform itself more or less rapidly (depending on the operating conditions) into a solid catalytic composition, in the presence of at least one liquid hydrocarbon phase, advantageously the reaction medium. Highly surprisingly, this solid catalytic composition retains its catalytic activity. Biphase catalysis thus becomes solid-liquid catalysis.

The solid catalytic composition obtained constitutes a further object of the invention.

The hydrocarbon phase advantageously contains the reactant (olefin), and/or at least one reaction product (oligomer). The organic phase can be introduced before, during or after the catalytic element, but preferably the catalytic element is added before the hydrocarbon phase or simultaneously therewith.

Thus the nickel compounds dissolved in the liquid mixture formed by the lithium halides with the hydrocarbylaluminium halides constitute, in the presence of oligomerisation products and/or in the presence of olefins, a heterogeneous-dispersed solid catalyst which is active for the oligomerisation or co-oligomerisation of mono-olefins.

A further object of the invention is to provide a process for the oligomerisation and co-oligomerisation of olefins, in which the olefin(s) are brought into contact with a nickel compound which is at least partially dissolved in the liquid mixture formed by lithium halides with hydrocarbylaluminium halides.

The hydrocarbylaluminium halides of the invention have general formula $Al_2X_xR_{6-x}$, where X is chlorine or bromine, R is an alkyl, cycloalkyl, aryl or aralkyl residue containing 1 to 10, preferably 2 to 6, carbon atoms, and x takes the values 2, 3 or 4. They can be used alone or as a mixture. Examples are alkylaluminium chlorides such as ethylaluminium dichloride, isobutylaluminium dichloride, ethylaluminium sesquichloride and diethylaluminium chloride.

The lithium halides of the invention are lithium chloride and/or lithium bromide.

In a preferred embodiment of the invention, the lithium halide, which has been dried by heating, is mixed separately with the hydrocarbylaluminium halide, which is pure or in the presence of a hydrocarbon. The compounds are used in an Al/Li molar ratio such that the mixture is liquid at the moment it the olefin is introduced.

This ratio is preferably greater than 1, advantageously in the range 1 to 4, more preferably in the range 1.5 to 3, for use at a temperature in the range 0° C. to 50° C. It is generally desirable to obtain a mixture which is liquid between −50° C. and +100° C.

The compounds of the catalytic element, in particular nickel, of the invention are preferably zerovalent, monovalent or divalent complexes, the latter of which may or may not contain one or two nickel-carbon bonds. Particularly desirable compounds are, among others, bivalent nickel salts such as the halides, the sulphate, the phosphate, the carboxylates, the acetylacetonates, the tetrahalogenoborates and complexes which form salts with amines, phosphines, ethers, nitriles, or esters, alone or as a mixture, and advantageously the mixture described in French patent application FR 93/11 382. Phosphines can be added to salts which do not contain phosphines. Examples are $NiCl_2$, $NiCl_2.2Pyridine$, $NiCl_2.2P(i-Pr)_3$, $NiCl_2.2P(Bu)_3$, $Ni(acetonitrile)_6(BF_4)_2$, nickel 2-ethylhexanoate, and nickel acetylacetonate.

The nickel compound can be introduced with a diluent, for example a hydrocarbon, preferably an aromatic hydrocarbon.

The compound of the catalytic element (nickel) is preferably mixed with the liquid composition obtained above in the presence of an olefin, for example the olefin which is to be catalytically oligomerised, in the presence or otherwise of a further hydrocarbon.

The concentration of the compound of the catalytic element (nickel) in the liquid mixture formed by at least one lithium halide and at least one hydrocarbylaluminium halide is advantageously in the range 1 mmole per liter to 500 mmoles per liter, preferably in the range 2 mmoles per liter to 200 mmoles per liter, more preferably in the range 2 mmoles per liter to 100 mmoles per liter, and most preferably in the range 2 mmoles per liter to 50 mmoles per liter.

Examples of olefins to which the process can be applied are ethylene, propylene, n-butenes and n-pentenes, either alone or as a mixture.

In the oligomerisation process, the olefin(s) can be used pure or diluted by saturated hydrocarbons such as those found in cuts from various hydrocarbon refining processes, such as ethane with ethylene, propane with propylene, and butanes with butenes.

The temperature at which oligomerisation is carried out is in the range −30° C. to 100° C., preferably in the range −10° C. to 50° C. The pressure can be in the range from atmospheric pressure or below atmospheric pressure to 10 MPa, preferably in the range from atmospheric pressure to 1 MPa, but will be sufficient to maintain at least a portion of the olefin(s) in the liquid phase.

Catalytic oligomerisation of olefins can be carried out in a closed system, a batch system or a continuous system with one or more reaction stages. At the reactor outlet, the hydrocarbon phase is separated from the solid phase then washed with water. The solid phase containing the catalyst and which is in the reactor is used again.

The following examples illustrate the invention without in any way limiting its scope.

EXAMPLE 1

Preparation of a lithium chloride - ethylaluminium dichloride liquid mixture 2.55 g (0.06 mole) of lithium chloride, which had been dried by heating under vacuum, was introduced into a 100 ml flask provided with an argon inlet and a magnetic stirrer. The flask was cooled to −30° C. and 14 ml (0.14 mole) of ethylaluminium dichloride was introduced. The system was slowly heated to ambient temperature and stirring was started. After 2 hours, a colourless liquid mixture was obtained.

Oligomerisation of propylene 64 mg (0.13 mmole) of nickel (II) hexaquis acetonitrile bis- tetrafluoroborate, 10 ml of heptane and 4 ml (17 mmoles based on lithium) of the above compound was introduced into a 150 ml capacity glass reactor provided with a stirring system and a double envelope for circulating a heat exchange medium, which reactor had been purged of air and moisture. The mixture formed two non miscible phases. The reactor temperature was adjusted to 5° C. and the propylene consumption was followed by the weight loss in the supply reservoir connected to the reactor via a pressure reducing valve. The products were periodically extracted and analysed. From the first extraction after one hour of reaction, the lower liquid composition transformed into a yellow solid. After an initial period of low propylene consumption, a productivity of 4.8 kg/g of nickel/hour was obtained. The products of the fourth extraction had the following composition:

| Selectivities (%) | | Selectivity in C6 fraction (%) | |
|---|---|---|---|
| C6 | 84 | 2-methyl-1-pentene | 4 |
| C9 | 15 | 2-methyl-2-pentene | 40 |
| C12+ | 1 | 4-methyl-1-pentene | 1 |
| | | 4-methyl-2-pentene | 30 |
| | | hexenes | 16 |
| | | 2,3-dimethyl-1-butene | 4 |
| | | 2,3-dimethyl-2-butene | 5 |

EXAMPLE 2

The method of Example 1 was followed, with the exception that the temperature was 10° C., with one atmosphere of 1-butene, and the 1-butene consumption was followed with time. After an initial period of low butene consumption, a productivity of 3.0 kg/g nickel/hour was attained. From the first extraction the lower composition transformed into a yellow solid. The products obtained were: 95±2% of directs (isooctenes); 5±2% of trimers ($C_{12}$) and small quantities of heavier products ($C_{16+}$). The products in the C8 fraction constituted a complex mixture of olefins which, after hydrogenation, turned out to be n-octane (6%), 3-methylheptane (58%) and 3,4-dimethylhexane (36%).

We claim:

1. A catalytic composition comprising at least one lithium halide, at least one hydrocarbylaluminium halide and at least one nickel compound.

2. A catalytic composition according to claim 1, in which the lithium halide is lithium chloride.

3. A catalytic composition according to claim 1, in which the lithium halide is lithium bromide.

4. A catalytic composition according to claim 1, in which the hydrocarbonaluminium halide is an alkylaluminium chloride.

5. A catalytic composition according to claim 4, in which the alkyl aluminium chloride compound is dichloroethylaluminium.

6. A catalytic composition according to claim 1, in which the molar ratio between the hydrocarbylaluminium halide and the lithium halide is greater than 1.

7. A catalytic composition according to claim 1, in which the nickel compound is a nickel salt.

8. A catalytic composition according to claims 1, in which the nickel compound is a zerovalent, monovalent or divalent complex.

9. A catalytic composition according to claim 1, in which the nickel compound is selected from the group consisting of the halides, the sulphate, the phosphate, the carboxylates, the acetylacetonates, the tetrahalogenoborates and complexes which form salts with amines, phosphines, ethers, nitriles and esters, either alone or as a mixture.

10. A catalytic composition according to claim 1, in which the nickel compound is $NiCl_2$, $NiCl_2.2Pyridine$, $NiCl_2.2P(i-Pr)_3$, $NiCl_2.2P(Bu)_3$, $Ni(acetonitrile)_6(BF_4)_2$, nickel 2-ethylhexanoate or nickel acetylacetonate.

11. A catalytic composition resulting from mixing at least one nickel compound with a liquid mixture formed by at least one lithium halide and at least one hydrocarbylaluminium halide.

12. A catalytic composition according to claim 11, in which the concentration of the compound(s) of nickel in the liquid mixture formed by at least one lithium halide and at least one hydrocarbylaluminium halide is in the range of 2 mmoles per liter to 200 mmoles per liter.

13. A solid catalytic composition obtained from a liquid mixture of at least one lithium halide with at least one hydrocarbylaluminium halide, then the introduction of at least one hydrocarbon phase and nickel, said solid catalyst separating from the liquid organic phase.

14. A solid catalytic composition according to claim 13, in which the hydrocarbon phase contains at least one reactant and/or at least one reaction product.

15. A solid catalytic composition according to claim 13, obtained from a liquid mixture of at least one lithium halide with at least one hydrocarbylaluminium halide, plus the addition of at least one nickel compound and introduction of a hydrocarbon phase before, during or after addition of the nickel, said solid catalyst separating from the liquid hydrocarbon phase.

16. In a process comprising subjecting an olefin to dimerisation in contact with a catalyst composition, the improvement wherein the catalyst composition is according to claim 1.

17. In a process comprising subjecting an olefin to codimerisation in contact with a catalyst composition, the improvement wherein the catalyst composition is according to claim 1.

18. In a process comprising subjecting an olefin to oligomerisation in contact with a catalyst composition, the improvement wherein the catalyst composition is according to claim 1.

19. In a process comprising subjecting an olefin to co-oligomerisation in contact with a catalyst composition, the improvement wherein the catalyst composition is according to claim 1.

* * * * *